(12) United States Patent
Whitten et al.

(10) Patent No.: US 8,455,265 B2
(45) Date of Patent: Jun. 4, 2013

(54) SURFACE GRAFTED CONJUGATED POLYMERS

(75) Inventors: David G. Whitten, Albuquerque, NM (US); Sireesha Chemburu, Albuquerque, NM (US); Thomas Corbitt, Albuquerque, NM (US); Linnea Ista, Albuquerque, NM (US); Gabriel Lopez, Albuquerque, NM (US); Kirk S. Schanze, Gainesville, FL (US); Motokatsu Ogawa, Sherman Oaks, CA (US); Eunkyung Ji, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 236 days.

(21) Appl. No.: 12/529,390

(22) PCT Filed: Feb. 29, 2008

(86) PCT No.: PCT/US2008/002756
§ 371 (c)(1),
(2), (4) Date: May 13, 2010

(87) PCT Pub. No.: WO2008/143731
PCT Pub. Date: Nov. 27, 2008

(65) Prior Publication Data
US 2011/0159605 A1  Jun. 30, 2011

Related U.S. Application Data

(60) Provisional application No. 60/892,350, filed on Mar. 1, 2007, provisional application No. 60/980,693, filed on Oct. 17, 2007.

(51) Int. Cl.
*G01N 33/552* (2006.01)
*G01N 33/543* (2006.01)

(52) U.S. Cl.
USPC ............. 436/527; 422/82.05; 422/82.06; 422/82.07; 422/82.08; 436/85; 436/86; 436/87; 436/88; 436/89; 436/90; 436/91; 436/92; 436/93; 436/94; 436/95; 436/96; 436/97; 436/98; 436/166; 436/172; 436/518; 436/523; 436/524; 436/525; 436/526; 436/528; 436/529; 436/530; 436/531

(58) Field of Classification Search
USPC ............. 422/82.05–82.08; 436/85–98, 164, 436/166, 172, 518, 523–531
See application file for complete search history.

(56) References Cited

U.S. PATENT DOCUMENTS 5,489,400 A * 2/1996 Liu et al. .................. 252/500
(Continued)

FOREIGN PATENT DOCUMENTS
WO  WO-2008143731 A2  11/2008

OTHER PUBLICATIONS
Gieselman, M. B. et al, Macromolecules 1993, 26, 5633-5642.*
(Continued)

*Primary Examiner* — Arlen Soderquist
(74) *Attorney, Agent, or Firm* — Schwegman, Lundberg & Woessner, P.A.

(57) ABSTRACT

A surface grafted conjugated polyelectrolyte (CPE) is formed by coupling a CPE by a coupling moiety to the surface of a substrate. The substrate can be of any shape and size, and for many uses of the surface grafted CPE, it is advantageous that the substrate is a nanoparticle or microparticle. Surface grafted CPEs are presented that use silica particles as the substrate, where a modified silane coupling agent connects the surface to the CPE by a series of covalent bonds. Two methods of preparing the surface grafted CPEs are presented. One method involves the inclusion of the surface being modified by the coupling agent and condensed with monomers that form the CPE in a grafted state to the substrate. A second method involves the formation of a CPE with terminal groups that are complimentary to functionality that has been placed on the surface of the substrate by reaction with a coupling agent. The surface grafted CPEs are also described for use as biosensors and biocides.

16 Claims, 11 Drawing Sheets

U.S. PATENT DOCUMENTS

| | | | |
|---|---|---|---|
| 6,743,640 | B2 | 6/2004 | Whitten et al. |
| 7,122,383 | B2 | 10/2006 | Jones et al. |
| 2003/0134959 | A1 | 7/2003 | Hancock et al. |
| 2003/0178607 | A1* | 9/2003 | Swager et al. ............... 252/582 |
| 2004/0241768 | A1 | 12/2004 | Whitten et al. |
| 2005/0059168 | A1* | 3/2005 | Bazan et al. ................. 436/518 |
| 2005/0148254 | A1 | 7/2005 | Lu et al. |
| 2006/0120923 | A1 | 6/2006 | Swager et al. |
| 2006/0175193 | A1 | 8/2006 | Inganas et al. |

OTHER PUBLICATIONS

Winkler, B. et al, Chemistry of Materials 1999, 11, 704-711.*
Jannasch, P., Macromolecules 2000, 33, 8604-8610.*
Zotti, G. et al, Chemistry of Materials 2001, 13, 43-52.*
Jiruo, Z. et al, Materials Letters 2002, 56, 543-545.*
Ballauff, M., Macromolecular Chemistry and Physics 2003, 204, 220-234.*
Bartholome, C. et al, Macromolecules 2003, 36, 7946-7952.*
Skaff, H. et al, Journal of the American Chemical Society 2004, 126, 11322-11325.*
Bartholome, C. et al, Macromolecules 2005, 38, 1099-1106.*
Fan, Q.-L. et al, et al, Macromolecules 2005, 38, 2927-2936.*
Lu, L. et al, Langmuir 2005, 21, 10154-10159.*
Achyuthan, K. E. et al, Journal of Materials Chemistry 2005, 15, 2648-2656.*
Kim, K. et al, Langmuir 2005, 21, 5207-5211.*
Yang, C. J. et al, Angewante Chemie International Edition 2005, 44, 2572-2576.*
Zhao, X. et al, Macromolecules 2006, 39, 6355-6366.*
Wang, X.-L. et al, Solid State Ionics 2006, 177, 1287-1291.*
Ogawa, K. et al, Langmuir 2007, 23, 4541-4548.*
Thomas, Samuel W. Chemical Reviews 2007, 107, 1339-1386.*
L. Arnt et al, Journal of the American Chemical Society 2002, 124, 7664-7665.*
Clark, A. P.-Z. et al, Nano Letters 2005, 5, 1647-1652.*
Tew, G. N. et al, Biochimica et Biophysica Acta 2006, 1387-1392.*
Tan C., et al., "Photophysics, aggregation and amplified quenching of a water-soluble poly (phenylene ethynylene)," *Chem. Commun.*, 2002, pp. 446-447.
Tan, C., et al., "Solvent-Induced Self-Assembly of a Meta-Linked Conjugated Polyelectrolyte. Helix Formation, Guest Intercalation, and Amplified Quenching," *Adv. Mater.*, Jul. 19, 2004, pp. 1208-1212, vol. 16, No. 14.
Wang, Ying, et al., "Membrane Perturbation Activity of Cationic Phenylene Ethynylene Oligomers and Polymers: Selectivity against Model Bacterial and Mammalian Membranes", Langmuir, 26(15), (2010), 12509-12514.

* cited by examiner

SURFACE GRAFTED CONJUGATED POLYMERS

CROSS-REFERENCE TO RELATED APPLICATIONS

The present application is the U.S. National Stage Application of International Patent Application No. PCT/US2008/002756, filed on Feb. 29, 2008, which claims the benefit of U.S. Application Ser. No. 60/892,350, filed Mar. 1, 2007, and claims the benefit of U.S. Application Ser. No. 60/980,693, filed Oct. 17, 2007, all of which are hereby incorporated by reference herein in their entirety, including any figures, tables, or drawings.

STATEMENT REGARDING FEDERALLY SPONSORED RESEARCH OR DEVELOPMENT

The U.S. Government has certain rights to the invention pursuant to Air Force Office of Scientific Research under Grant No. FA9550-04-1-0161, Defense Threat Reduction Agency under Grant No. W-911-NF-07-1-0079, and Office of Naval Research under Grant No. N00014-05-V-0743.

FIELD OF THE INVENTION

The invention relates to a method to prepare and compositions of conjugated polymers grafted to surfaces and their use as biosensors and biocides.

BACKGROUND OF THE INVENTION

Water-soluble conjugated polyelectrolytes (CPEs) display strong photoluminescence and rapid transport of a singlet exciton along the π-conjugated backbone. Significant attention has been focused on amplified quenching of the CPE fluorescence by ionic quenchers. Amplified quenching effects have been demonstrated with quenchers that operate by either electron transfer or energy transfer mechanisms. In some CPE-quencher systems, Stern-Volmer constants for amplified quenching can be as large as $10^8$ $M^{-1}$. This highly efficient quenching in CPE-quencher systems has been attributed to ion pairing between CPE chains and oppositely charged quenchers and a rapid intrachain transport of the exciton. The large quenching response displayed by CPEs has led to their application in highly sensitive fluorescence-based sensors for biological targets. Some assays also have utilized layer-by-layer (LbL) coated latex or silica nano- and microcolloids in combination with quencher-tether-ligand (QTL) or lipid bilayer assemblies to fix CPEs to a surface.

Examples of polymer grafted colloids and surfaces have been reported which are fabricated by using surface initiated living polymerization reactions, such as atom transfer radical polymerization (ATRP) and nitroxide mediated radical polymerization (NMRP). Although conjugated polymer LbL coated silica particles and conjugated polymer silica composites are known, a general method for preparation of silica particles that are surface-grafted with a conjugated polymer is not available. Beinhoff et al., *Langmuir* 2006, 22, 2411-14 discloses the preparation of a polyfluorene-based conjugated polymer grafted surface based on a Ni(0)-mediated step-growth polymerization reaction. By this approach, a silica substrate is modified with a cross-linked polymethacrylate network containing an aryl halide group. The aryl halide units serve as grafting points for a polyfluorene produced by a Ni(0) mediated step-growth polymerization reaction.

A general method for the grafting of a CPE to a surface, would allow the development of applications to these polymeric systems. Fluorescence sensing is one example of an application that can use surface grafted CPEs. Another application for the grafted CPEs is that of biocidal active agents.

SUMMARY OF THE INVENTION

The invention is directed to a surface grafted conjugated polyelectrolyte (CPE), where a solid substrate has at least one CPE attached to the substrate's surface by a coupling moiety that forms an ionic or, preferably a covalent bond to the surface and a covalent bond to the CPE. The substrate can be a nanoparticle or a microparticle such as a metal oxide, a metal, a semiconductor, carbon, or a polymer. A useful substrate is silica particles. The CPE can be any polymer with a conjugated backbone that contains some ionic side groups to promote an affinity with water. The conjugated backbone can be that of poly(phenylene ethynylene) or poly(phenylene vinylene) which can have ionic side groups attached to the phenyl units of the backbone. Other side groups can be present on the polymer, including oligo(ethylene oxide) groups which further enhance the water affinity of the CPE. The coupling moiety can have a surface bound silyl group linked by a chain of 1 to 12 atoms to a terminal aromatic unit of the CPE. Various surface grafted CPEs of the invention are silica particles that have coupling moieties derived from aminopropyltrimethoxysilane and CPEs of the following structures:

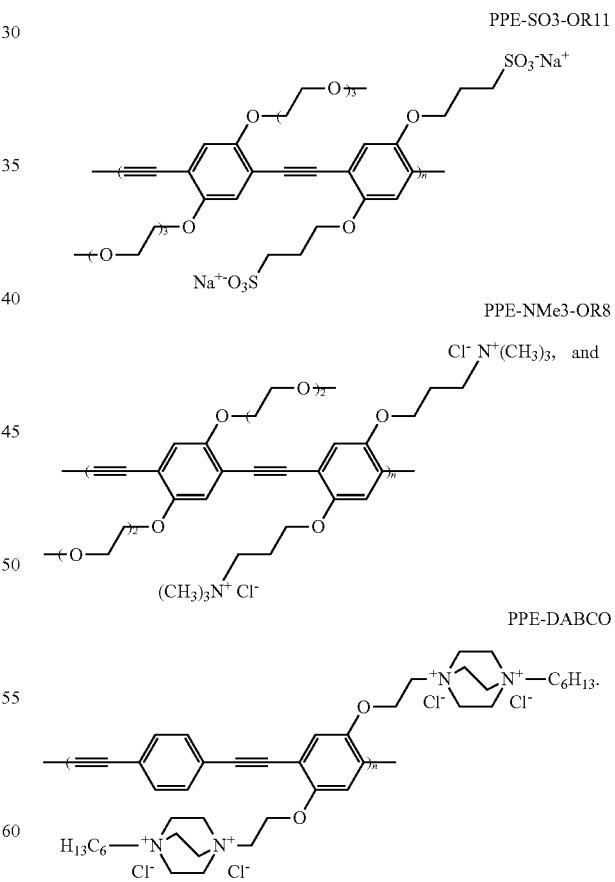

The invention is also directed to a method of preparing the surface grafted CPEs where a substrate with reactive sites on the surface is treated with a coupling agent that has arylhalide, alkene or alkyne groups, which can condense with at least some of the reactive functionality in a mixture of monomers that form a CPE and has groups to condense with the reactive sites on the surface. The surface grafted CPE is formed from the monomers and attached to the surface upon polymerization. The coupling agent can be 4-iodo-N-[3-(trimethoxysilyl)propyl]-benzamide and the monomers can be disodium, 2,5-diiodo-1,4-bis(3-sulfonatopropoxy)benzene and 1,4-diethynyl-2,5-bis[2-[2-(2-methoxyethoxy)-ethoxy]ethoxy]benzene that yields PPE-SO3-OR11. Alternate pairs of monomers can be: 2,5-diiodo-1,4-bis(3-(N,N,N-trimethylammonium)propoxy)benzene, dichloride and 1,4-diethynyl-2,5-bis[2-(2-methoxyethoxy)ethoxy]benzene which yields PPE-NMe3-OR8; 2,5-diiodo-1,4-bis(3-(4-hexyl-1,4-diazabicyclo[2.2.2]octane-yl)propoxy)benzene, tetrachloride and 1,4-diethynylbenzene which yields PPE-DABCO; or any substituted 1,4-diethynylbenzene and 1,4-diiodobenzene where one or more hydrogens on at least aromatic ring of a monomer is substituted with an ionic group. In general a catalyst for the condensation reaction is included in the reaction mixture and also a solvent is employed during all reactions.

A second method of preparing a surface grafted CPE involves reaction of a provided substrate with reactive sites on its surface with a coupling agent where the coupling agent has a reactive functionality that is complementary to a reactive functionality on the termini of a CPE, where reaction of the coupling agent functionalized surface and the reactive CPE forms the surface grafted CPE. The reactive functionality can be those from an excess of the two monomers or can be of a monomer that is effectively a monofunctional, end-capping, monomer with respect to the polycondensation reaction that forms the CPE to be grafted to the surface. For example a surface can be functionalized with aminopropyltrimethoxysilane and subsequently reacted with a CPE with carboxylic acid groups grafting the CPE to the surface by an amide bond. For example, such a carboxylic acid terminated CPE can have the structure:

surface grafted CPE can occur in the dark, but can also be active only when irradiated with light.

BRIEF DESCRIPTION OF THE DRAWINGS

There is shown in the drawings embodiments which are presently preferred, it being understood, however, that the invention can be embodied in other forms without departing from the spirit or essential attributes thereof.

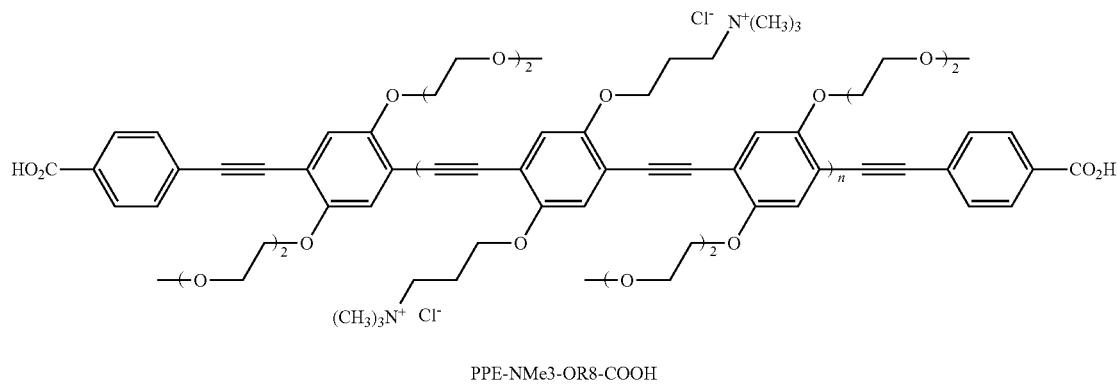

PPE-NMe3-OR8-COOH

Figure 9:
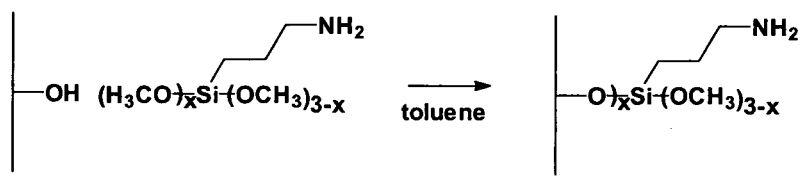

The invention is also direct to the use of the surface grafted CPE as a component of a biosensor, where in addition to the surface grafted CPE, the sensor includes a compound with a recognition element for a target biological agent linked to a fluorescence quenching element. The quenching element inhibits fluorescence of the CPE when complexed to the CPE but, when in the presence of a target biological agent, the quenching element is preferentially bound to the target allowing the CPE to fluoresce to indicate the presence of the target agent. Another embodiment of the invention is to use the surface grafted CPE as a biocide, where the CPE can exhibit activity to one or more biological agent. The activity of the FIG. 9 shows the preparation of an amine functionalized surface by reaction with a silane coupling agent, according to an embodiment of the invention.

Figure 10:
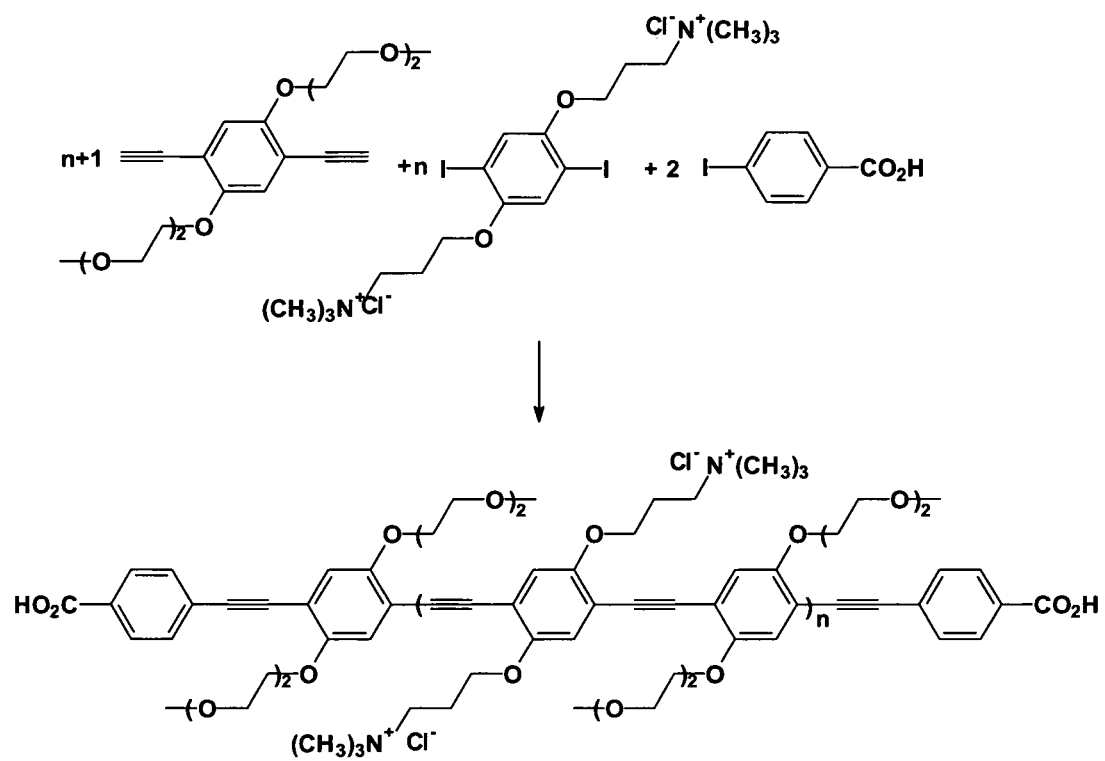

FIG. 10 shows the preparation of a dicarboxylic terminated CPE, according to an embodiment of the invention.

Figure 11:
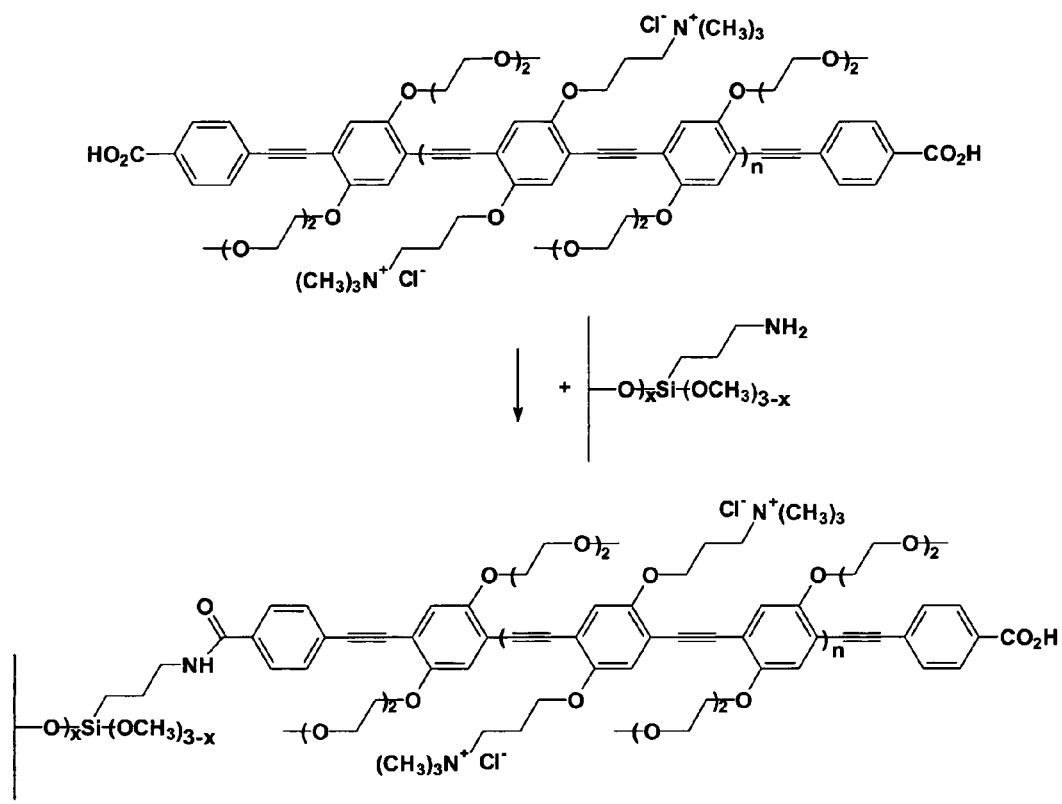

FIG. 11 shows the preparation of a CPE functionalized surface having cationic side groups by reaction of an amine functionalized surface with a dicarboxylic terminated CPE according to an embodiment of the invention.

Figure 12:
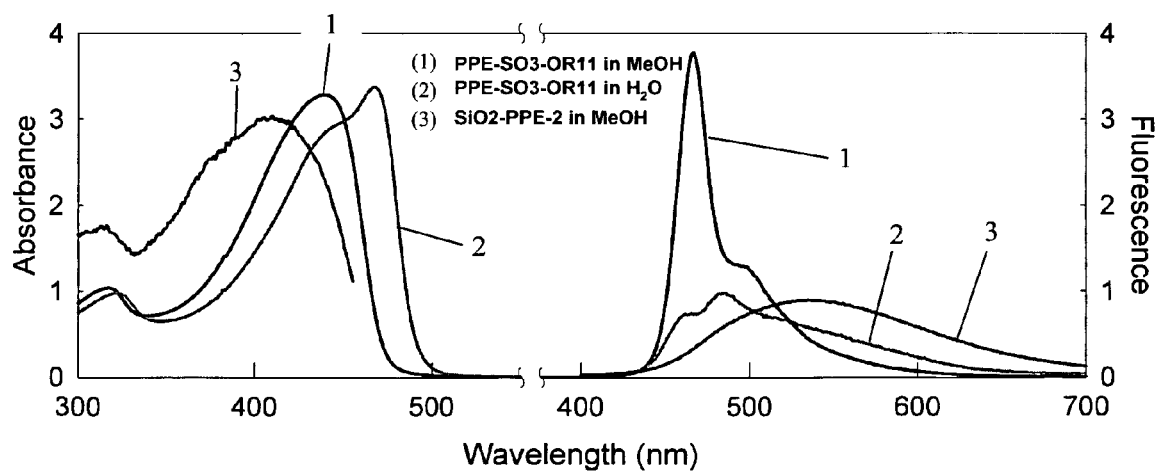

FIG. 12 shows the Absorption and Emission spectra of PPE-SO3-OR11 and SiO2-PPE.

Figure 13:
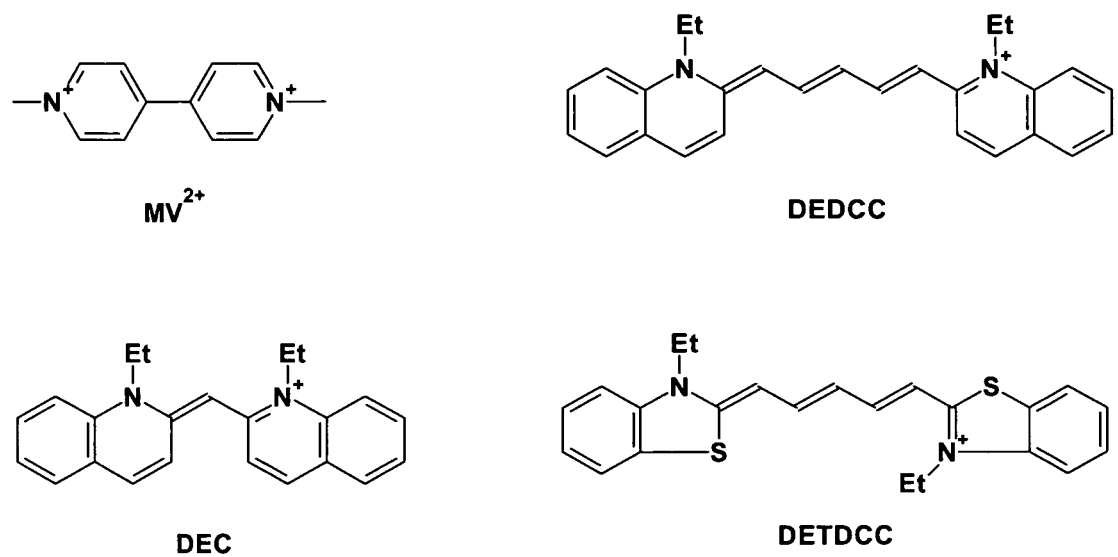

FIG. 13 shows the structures of fluorescence quenchers used to probe the fluorescence quenching of the CPE functionalized silica particle SiO2-PPE.

Figure 14A:
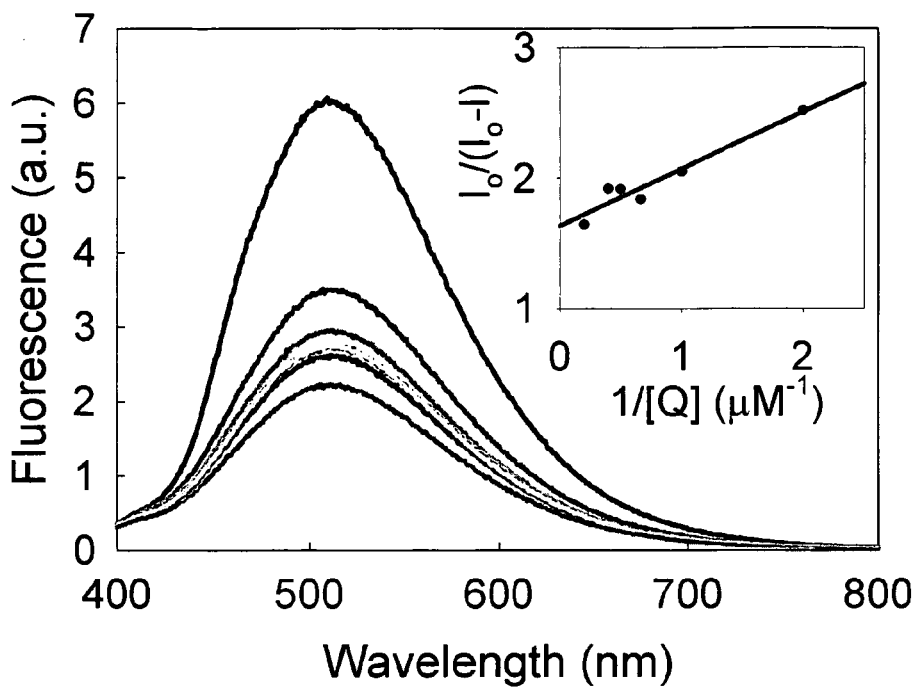
Figure 14B:
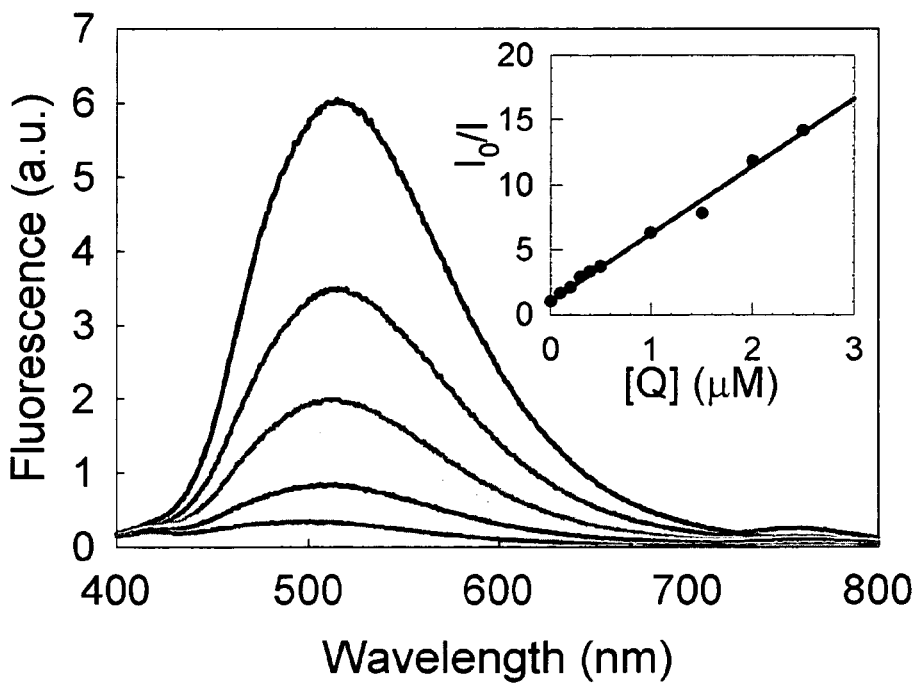

FIG. 14 shows the Stern-Vohner quenching of SiO2-PPE-2 suspended in water using (a) an electron-transfer quencher and (b) an energy-transfer quencher.

Figure 15A:
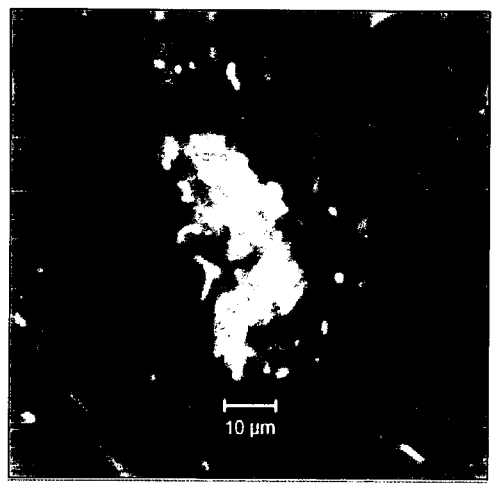
Figure 15B:
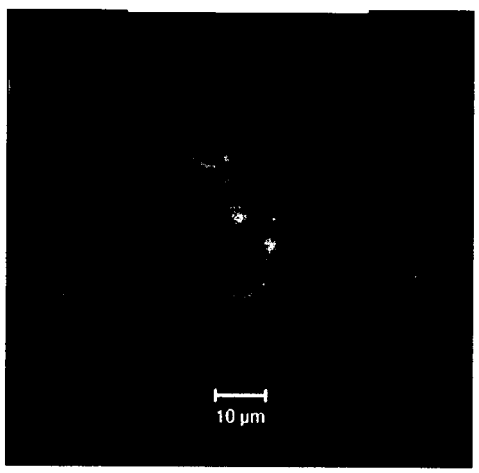
Figure 15C:
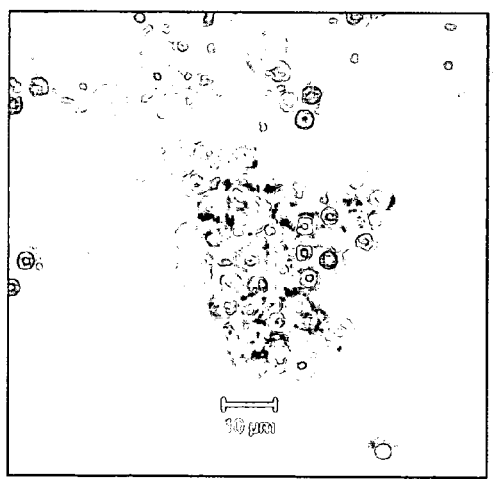

FIG. 15 shows microscope images of CPE grafted silicon microspheres exposed to *Cobetia marina* and broad spectrum light from a halogen lamp for 15 minutes where 15(a) shows the dead bacteria by the intensity of bacteria that fluoresces green after exposure to a dye, 15(b) shows the live bacteria by the intensity of bacteria that fluoresces red after exposure to a dye, and 15(c) shows the agglomerations of the microspheres that typically follows light enhanced biocidal activity.

Figures 16A, 16B:
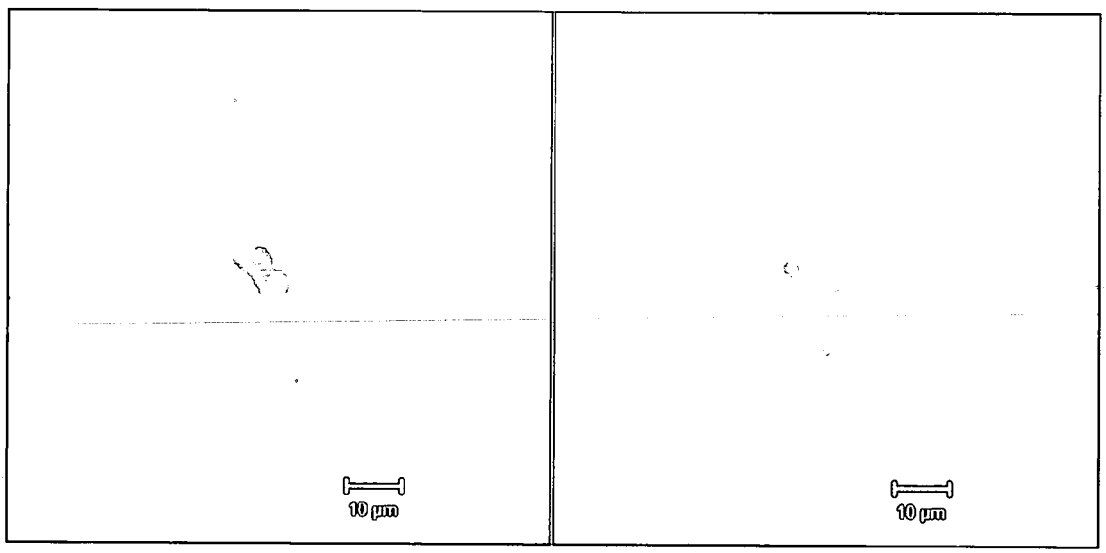

FIG. 16 shows microscope images of CPE grafted silicon microspheres exposed to *Cobetia marina* in the dark where 16(a) shows the dead bacteria by the intensity of bacteria that fluoresces green after exposure to a dye and 16(b) shows the live bacteria by the intensity of bacteria that fluoresces red after exposure to a dye.

DETAILED DESCRIPTION

The present invention is directed to surface grafted conjugated polyelectrolytes (CPEs). In one embodiment the surface grafted CPE has at least one negatively charged group on at least one repeating unit of the CPE. In another embodiment the surface grafted CPE has at least one positively charged group on at least one repeating unit of the CPE. The surface to which the CPEs are bound can be a surface of any solid to which the CPE can be constrained to the surface via a coupling moiety which is bound covalently to the CPE and can be bound to the surface either covalently or ionically. The surface can be of a macroscopic article, such as a sheet, a fiber or a particle. The surface can also be that of a microscopic article such as a micro or nanoparticle. In an embodiment of the invention, surface grafted CPEs are used as a fluorescence sensor, and can be a biosensor. In another embodiment of the invention, the surface grafted CPEs are used as a light activated or dark active biocide.

The surface grafted CPEs can be those where a CPE is attached to a surface, the surface can be that of: a metal oxide, such as silica or titania; a metal surface, such as gold or silver functionalized with a reactive thiol; a semiconductor, such as Si, GaAs, CdSe, CdTe, and CdS; carbon; or a polymer, such as an acrylate, epoxy or siloxane. The CPE can be attached to the surface by a coupling moiety covalently bound to the CPE at an end of the CPE. The surface is attached to the coupling moiety by a covalent or ionic bond. The CPE is any polymer with a potentially fully conjugated backbone that contains ionic side groups to promote water miscibility. Among appropriate conjugated polymers to provide the backbone of CPEs, are derivatives of poly(paraphenylene), poly(phenylene vinylene), poly(phenylene ethynylene), poly(thiophene), poly(pyrrole), and poly(fluorine), and copolymers thereof.

Figure 1:
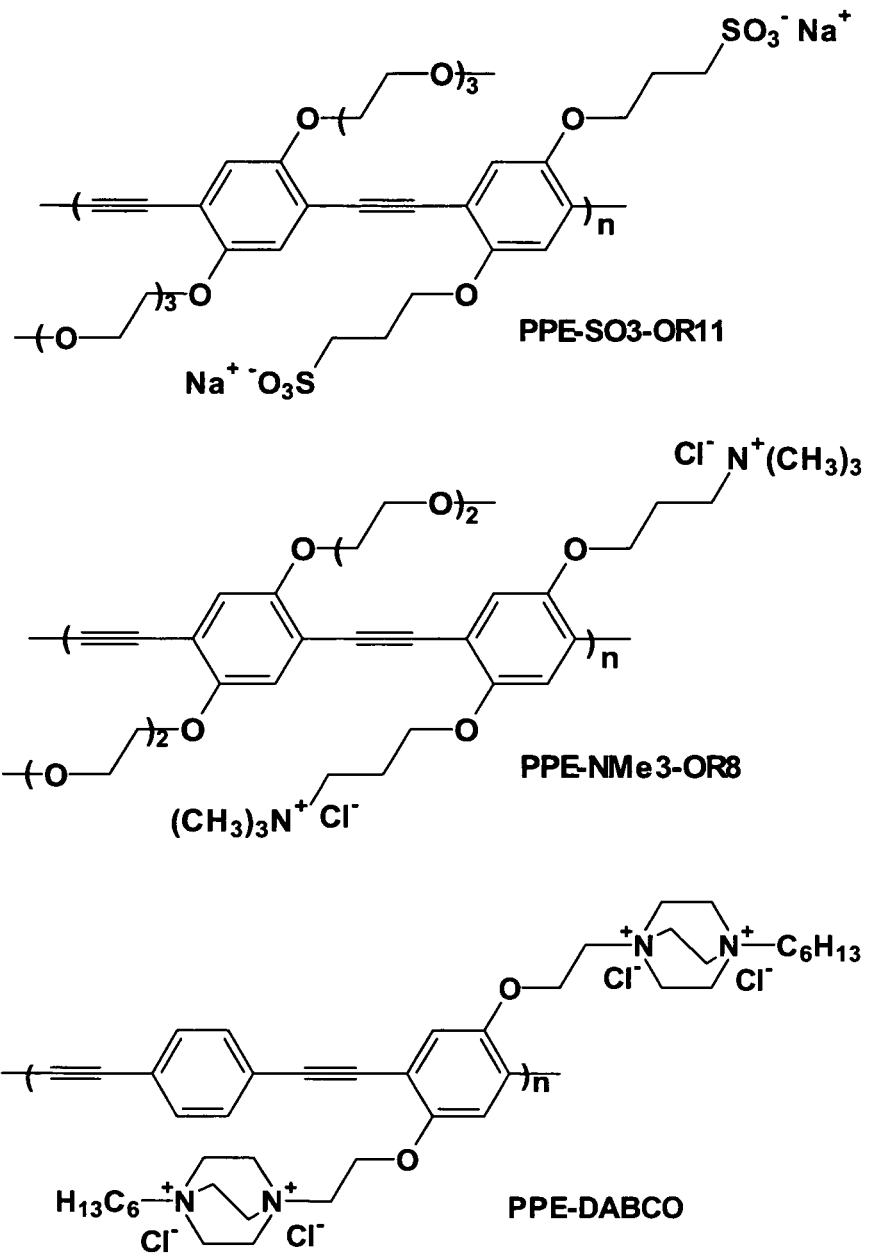
FIG. 1 shows the structure of three exemplary CPEs that can be coupled to a surface, according to embodiments of the invention.
Figure 3:
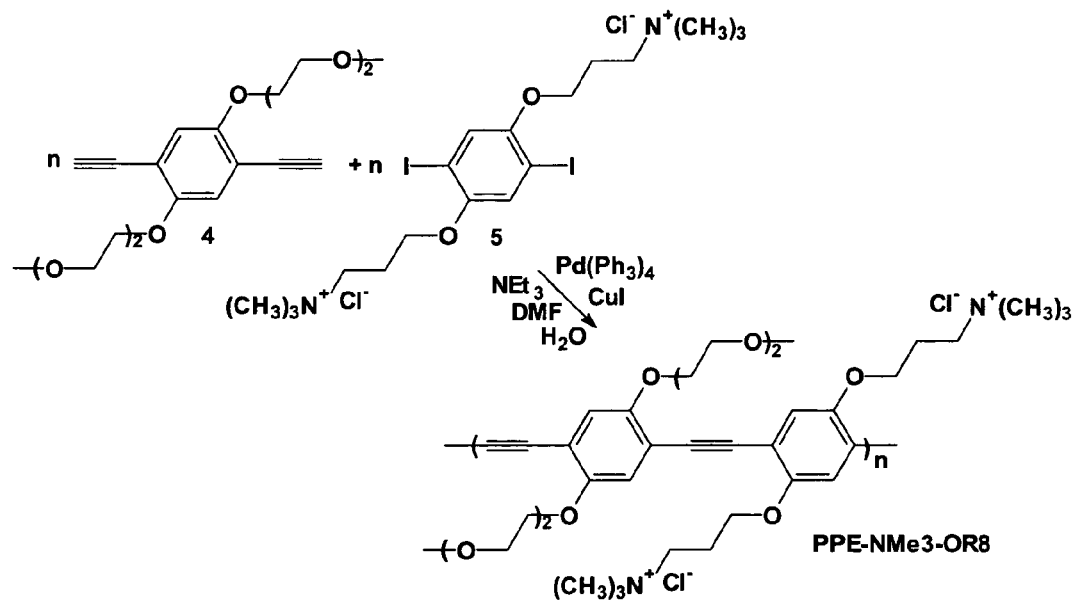
FIG. 3 shows the polymerization of two monomers to prepare a CPE with cationic side groups and oligo(ethylene oxide) side groups, according to an embodiment of the invention.
Figure 4:
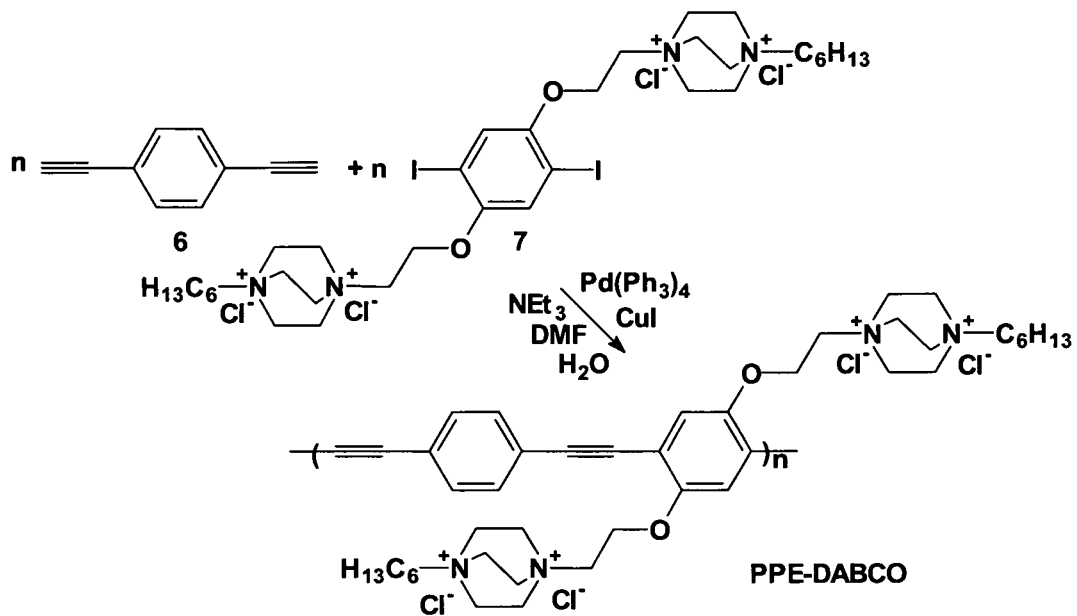
FIG. 4 shows the polymerization of two monomers to prepare a CPE with dicationic, DABCO, side groups, according to an embodiment of the invention.

In embodiments of the invention, polymers with the conjugated backbone can be a poly(phenylene vinylene) or a poly(phenylene ethynylene). Side groups are present with a sufficient number of the repeating units that are ionic to provide the desired miscibility with water. The side groups can be those that contain an anionic unit, for example the conjugate base of an acid such as an alkali metal salt of an organosulfonic acid. The side groups can be those that contain a cationic unit, for example, tetraalkylammonium halides or 4-diazabicyclo[2.2.2]octane (DABCO), which is a dicationic unit. Additional side groups can be other groups with affinity for water, such as oligomers of polyethylene oxide. Specific examples of three CPEs that can be grafted to a surface are illustrated in FIG. 1, where one has anionic side groups and oligoether side groups, a second CPE has cationic side groups and oligoether side groups, and the third CPE has DABCO side groups. Synthetic routs to these polymers are given in FIGS. 2 through 4. Additionally, the polycondensation can include complementary monomers, which leads to a homopolymer that has ionic groups on every repeating unit, or includes three or more monomers such that a random or semi-random copolymer in addition to the polymerizations that result in the alternating copolymers shown in FIG. 1.

The invention is also directed to methods for the grafting of a CPE on a surface. In one embodiment of the invention, the method can begin with a step to functionalize a surface and a subsequent step of using the surface functionality as a comonomer for the polymerization of a CPE. In another embodiment the method can begin with a step for the formation of a CPE with functional groups on at least one termini of the CPE that can be coupled to a surface having a complementary functional group to form a covalent or ionic bond in a subsequent step. The surface of a given material can inherently contain the complementary functional group, or can be a functional group that has been formed on a surface of a material prior to reaction with a terminal group of the CPE.

Figure 5:
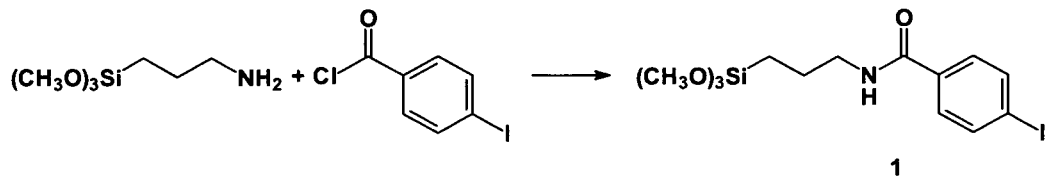
FIG. 5 shows the preparation of an ArI containing silane coupling agent, according to an embodiment of the invention.
Figure 7:
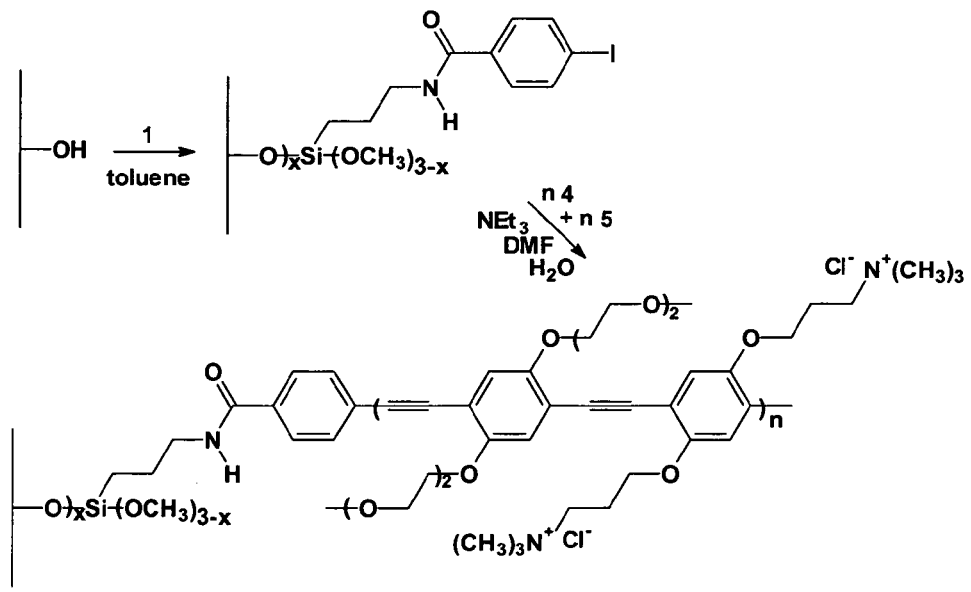
FIG. 7 shows the preparation of a CPE functionalized surface having cationic side groups by copolymerization with ArI functionalized surface, according to an embodiment of the invention.
Figure 8:
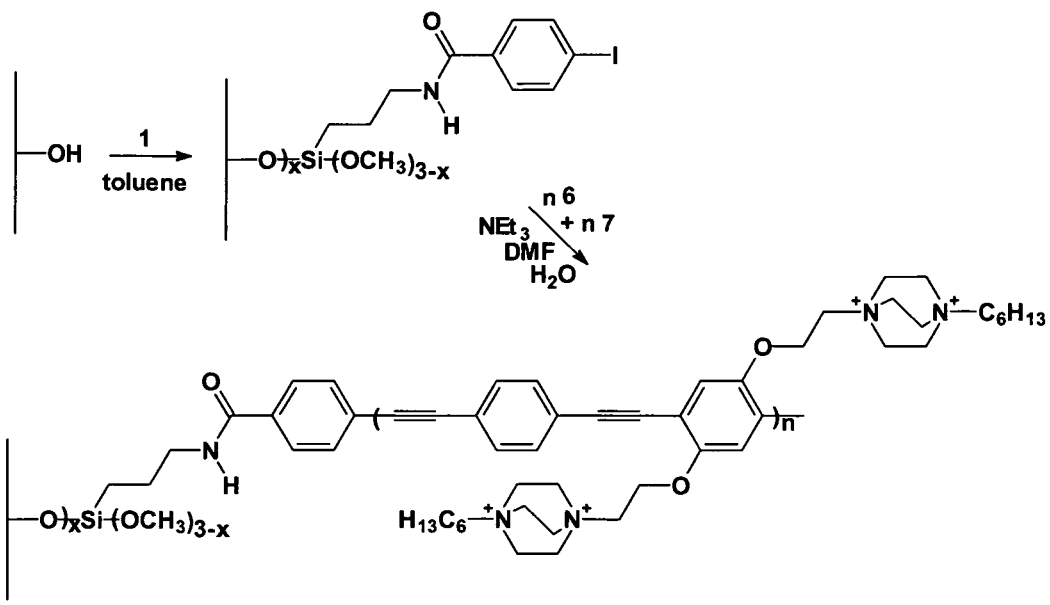
FIG. 8 shows the preparation of a CPE functionalized surface having dicationic, DABCO, side groups by copolymerization with ArI functionalized surface, according to an embodiment of the invention.

In one embodiment of the inventive method, a reactive aryl halide (ArX) functional group, an alkene group or an alkyne group is bonded onto a surface. Where an ArX group is used, the preferred halide is iodide, but can be bromide or chloride in some cases. For a silica surface, or other surfaces, the attachment to the surface can be carried out via a silane coupling agent containing the ArX functional group, where the preparation of a specific ArI containing coupling agent is illustrated in FIG. 5. The silica surface can include the surface of a nano- or micro-particle. In addition to silica surfaces, the surface to be modified can also be other metal oxide surfaces, such as titania, a metal surface, such as gold or silver functionalized with a reactive thiol, a semiconductor, such as Si, GaAs, CdSe, CdTe, and CdS, carbon, or a polymer, such as an acrylate, epoxy or siloxane. The ArI functional surface can be included into the polymerization mixture for the condensation between a diiodo substituted aromatic monomer and a dialkenyl or dialkynyl substituted aromatic monomer. This approach is illustrated in FIGS. 6 through 8 for three specific examples.

In an embodiment for the modification of a silica surface 3-aminopropyltrimethoxysilane (APTS) was treated with 4-iodobenzoyl chloride to yield a silane coupling agent with an ArI functionality by the formation of an amide bond, as shown in FIG. 5. The ArI functionality is then attached via the coupling agent to a silica surface via a series of covalent bonds by condensation of the methoxy groups of the coupling agent with the hydroxy groups of the silica surface to yield methanol and a Si—O bond as shown in the first step of FIGS. 6 through 8. The silane coupling agent must have at least one group attached to the Si atom that can be hydrolyzed and condensed with a surface that contains nucleophilic oxygens, such as silanol groups on a silica surface. In general, three groups are found on the coupling agent that can ultimately condense to the surface. FIGS. 6 through 9 display uncondensed groups as alkoxy groups, however, these groups can be, and frequently are silanol groups where hydrolysis has occurred but condensation has not occurred. Furthermore, two or more coupling agents may form one or more siloxane bonds between them where two or more coupling agents can be attached to a single site on the surface. Such variation on the grafting structure would be appreciated by those skilled in the art.

Figure 6:
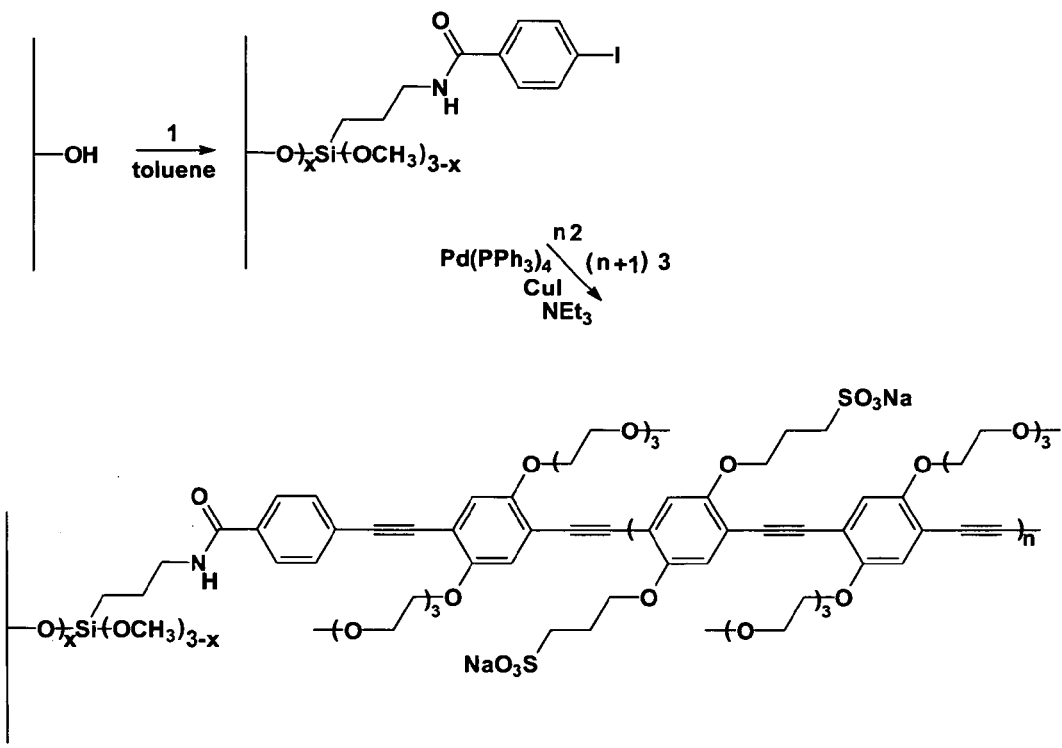
FIG. 6 shows the preparation of a CPE functionalized surface having anionic side groups by copolymerization with ArI functionalized surface, according to an embodiment of the invention.

In an embodiment of the invention, the solution polymerization of disodium, 2,5-diiodo-1,4-bis(3-sulfonatopropoxy) benzene and 1,4-diethynyl-2,5-bis[2-[2-(2-methoxyethoxy)-ethoxy]ethoxy]benzene in the presence of the ArI functional particles and catalyst, CuI and Pd[P($C_6H_5$)$_3$]$_4$, can be carried out under Sonogashira conditions in a dilute solution, DMF and water, and in the presence of an acid neutralization agent such as, triethylamine, to yield silica particles with multiple CPE attached thereon, as shown in FIG. 6. The stoichiometry of the monomers with complementary functionality can be, and generally is, other than a ratio of 1. A stoichiometric imbalance permits the control of the molecular weight of the CPE and allows many to all of the effective ends of the CPE to have a complementary functionality to that of the functionalized surface.

Other, monomers, solvents, catalyst, and other agents can be used in addition to or in place of the exemplary monomers, solvents, catalysts, and acid neutralization accepting agent, as would be appreciated by one skilled in the art and would not deviate from the invention. Other types of step-growth polymerization reactions that may be employed, in addition to that of Sonogashira, include Heck, Suzuki, and Yamamoto conditions. The resulting polymer can be characterized by $^1$H NMR and viscometry. The degree of polymerization, coupling of particles, and polymer dispersivity can vary with the nature and concentration of the monomers employed. Although the exemplary monomers do not produce cyclic oligomers, a low content of cyclic oligomers is possible with some monomers that can be employed in the practice of the invention. The CPE attached particles are typically isolated as a solid by common techniques such as filtration or centrifugation, and can be washed of any soluble, unbound oligomers of polymers, solvents and any side products or unconverted reagents.

In another embodiment of the inventive method, a surface, for example that of a silica particle, is modified with the silane coupling agent, 3-aminopropyltrimethoxysilane, as shown in FIG. 9. To the amine functionalized surface is added a CPE containing terminal carboxylic acid groups, where the preparation of the carboxylic acid terminal CPE is illustrated in FIG. 10. The grafting occurs by the formation of an amide bond between the amine functional surface and the acid terminal CPE. Dicyclohexylcarbodiimide (DCC) was used to promote amide bond formation.

In another embodiment of the invention the surface grafted CPEs can be used as a fluorescence sensor. The surface grafted CPE can be incorporated into sensors, such as biosensors, by the incorporation of appropriate ancillary species such as a fluorescence quencher and/or: a molecular or biomolecular recognition element; an enzyme; a nucleic acid; a polynucleic acid (e.g., DNA or RNA); an amino acid; a peptide; a glycopeptide; a carbohydrate; a polysaccharide; a lipid; a glycolipid; a micelle; a vesicle; a molecular beacon; or an aptamer. For example a biosensor can be constructed with these CPE modified surfaces and a fluorescence quenching moiety tethered to a biological agent recognition moiety. The general structure of such tethered quenchers and their use with non-covalently bound fluorescent polymers are disclosed in Whitten et al., U.S. Pat. No. 6,743,640, and can be used with the CPE modified surfaces of the present invention.

The CPE functionalized surfaces can be used for the preparation of biosensors. A receptor moiety for a given microbial agent can be linked to a fluorescence quench. In this manner the fluorescence of the CPE constrained to the surface is absent or low until the presence of microbial agent is present in the system. By the binding of the receptor to the microbe, the linked fluorescence quencher is modified in its position relative to the CPE, or removed from the proximity of the CPE, to an extent that the fluorescence increases significantly. The CPE modified surface can be that of particles suspended in an aqueous solution or deposited on a substrate, such that the presence of a microbial agent can be readily detected. The surface can be fabricated in a manner that the fluorescence can be readily viewed, and deposited in a manner that its exposure to the microbial agent can act as a warning for those in the proximity of the sensor.

The novel CPE modified surface can be used for its light activated biocidal properties. Non-covalently bound CPEs are known to display biocidal properties when irradiated with light and fluorescing. Biological agents to which the CPE can act as light activated biocides are disclosed in Lu et al., U.S. Patent Application Publication 2005/0148254 and these and other biological agents can be destroyed or inhibited by the surface grafted CPEs of the present invention.

The surface grafted CPEs can be used for the preparation of a light activated biocide. Additionally, many of the surface grafted CPEs can act as biocides in the dark. The surface grafted CPEs biocide can be deposited on a fabric or other surface such that in the presence of ambient light, even that of relatively low intensity, the fluorescing CPE functionalized surface can destroy a biological agent or a variety of biological agents.

The preparation of the CPE modified surfaces and their fluorescence and the quenching of the florescence, which can be exploited for the construction of biosensors and light activated biocidal agents, are illustrated in the following non-limiting examples.

EXAMPLES

All chemicals used for synthesis were of reagent grade and purchased from Sigma-Aldrich Chemical Company. Uniformly sized silica microspheres were purchased from Bangs Lab as a dry powder. Unless otherwise noted, chemicals and reagents were used without further purification. Reactions were carried out under a nitrogen atmosphere using freshly distilled solvents.

Unless otherwise noted, $^1$H and $^{13}$C NMR spectra were recorded on either a Varian Gemini 300 or VXR 300 spectrometer, and chemical shifts are reported in ppm relative to TMS. Infrared spectra were obtained using KBr pellets on a Perkin-Elmer Spectrum One FTIR Spectrometer. Measurements were automatically corrected for water and carbon dioxide. Thermogravimetric analysis (TGA) data was obtained with a Perkin-Elmer 7 series thermal analysis system. UV-visible absorption spectra were obtained on a Perkin-Elmer Lambda 25 dual beam absorption spectrometer using 1 cm quartz cells. Steady-state fluorescence emission spectra were recorded on a SPEX TRIAX 180 spectrograph coupled with a Spectrum One CCD detector. Steady-state fluorescence excitation spectra were recorded on SPEX FluoroMax spectrophotometer.

Example 1

4-Iodo-N-[3-(trimethoxysilyl)propyl]-benzamide (1) was prepared, as illustrated in FIG. 5, where a solution of 3-aminopropyltrimethoxysilane (1.78 mL, 10 mmol) in 10 mL of dichloromethane was added dropwise to a suspension of 4-iodobenzoyl chloride (1.33 g, 5 mmol) in 20 mL of dichloromethane at 0° C. The mixture was stirred for 1 hour and solvent was evaporated in vacuo. The residue was purified by column chromatography on silica using 2% methanol in chloroform. The solvent was removed by rotary evaporation to give a viscous oil. $^1$H NMR (300 MHz, CDCl$_3$): δ 0.70 (t, J=8.1 Hz, 2H), 1.73 (m, 2H), 3.42 (m, 2H), 6.64 (br, 1H), 7.49 (d, J=8.7 Hz, 2H), 7.76 (d, J=8.7 Hz, 2H). $^{13}$C NMR (75 MHz, CDCl$_3$): δ 6.81, 22.78, 42.54, 50.89, 98.41, 128.78, 134.44, 137.91, 167.03. HRMS calculated for $C_{13}H_{20}INO_4Si$ 409.0206, found 410.0295 (MH$^+$).

Example 2

2,5-Diiodo-1,4-bis(3-sulfonatopropoxy)benzene (2) of FIG. 2, was synthesized in the following manner adapted from Tan et al., *Chem. Commun.* 2002, 446-7. A solution of diiodohydroquinone (5.79 g, 16 mmol) in 100 mL of THF was added dropwise into a solution of NaH (60% in oil, 1.6 g, 40 mmol) in 300 mL of THF at 0° C. After 20 minutes of stirring, a solution of 1-(2-bromoethoxy)-2-(2-methoxyethoxy)ethane (9.08 g, 40 mmol) in 50 mL THF was added dropwise. The mixture was refluxed for 2 hours. After cooling of the mixture, a small amount of water was added and solvent was removed in vacuo. The residue was extracted with dichloromethane and washed with brine. After evaporation of the solvent, product was purified by column chromatography on silica using 1:1 mixture of ethyl acetate and hexane. Solvent was removed by rotary evaporation to give 1,4-diiodo-2,5-bis[2-[2-(2-methoxyethoxy)ethoxy]ethoxy]benzene as a yellow oil. $^1$H NMR (300 MHz, CDCl$_3$): δ 3.38 (s, 6H), 3.55 (m, 4H), 3.66 (m, 8H), 3.79 (m, 4H), 3.88 (m, 4H), 4.10 (m, 4H), 7.23 (s, 2H). $^{13}$C NMR (75 MHz, CDCl$_3$): δ 59.48, 70.04, 70.73, 71.02, 71.18, 71.58, 72.39, 86.85, 123.91, 153.51.

1,4-Diiodo-2,5-bis[2-[2-(2-methoxyethoxy)ethoxy]ethoxy]benzene (6.54 g, 10 mmol), trimethylsilylacetylene (3.1 mL, 22 mmol), CuI (57 mg, 0.3 mmol), and Pd(PPh3)4 (0.35 g, 0.3 mmol) were dissolved in 100 mL of diisopropyl amine and refluxed overnight. Water was added and the mixture was extracted with ether followed by several washings with water. Solvent was removed in vacuo. The product 1,4-bis[(trimethylsilyl)ethynyl]-2,5-bis[2-[2-(2-methoxyethoxy)ethoxy]ethoxy]benzene was purified by column chromatography on silica using 7:3 mixture of ethyl acetate and hexane. Solvent was removed by rotary evaporation to give white solid. $^1$H NMR (300 MHz, CDCl$_3$): δ 0.23 (s, 18H), 3.36 (s, 6H), 3.53 (m, 4H), 3.65 (m, 8H), 3.78 (m, 4H), 3.85 (m, 4H), 4.11 (m, 4H), 6.87 (s, 2H). $^{13}$C NMR (75 MHz, CDCl$_3$): δ 0.168, 59.24, 69.74, 69.91, 70.76, 71.00, 71.38, 72.16, 100.59, 101.06, 114.40, 117.98, 154.10.

1,4-bis[(trimethylsilyl)ethynyl]-2,5-bis[2-[2-(2-ethoxyethoxy)ethoxy]ethoxy]benzene (0.595 g, 1 mmol) was dissolved in 20 mL of THF and 10 mL of methanol. To the solution, 8 mL of 1M NaOH(aq) was added and refluxed for 2 hours. Water was added to the mixture and extracted with ether. The organic layer was washed with water several times, and then dried with Na2SO4. Solvent was removed by rotary evaporation to give 1,4-diethynyl-2,5-bis[2-[2-(2-methoxyethoxy)ethoxy]ethoxy]benzene (3), shown in FIG. 2, as a reddish solid. 1H NMR (300 MHz, CDCl$_3$): d 3.32 (s, 2H), 3.36 (s, 6H), 3.53 (m, 4H), 3.65 (m, 8H), 3.75 (m, 4H), 3.85 (m, 4H), 4.13 (m, 4H), 6.98 (s, 2H). $^{13}$C NMR (75 MHz, CDCl$_3$): d 59.46, 69.96, 70.03, 71.00, 71.15, 71.50, 72.39, 80.00, 83.22, 114.02, 118.75, 154.49.

Example 3

Figure 2:
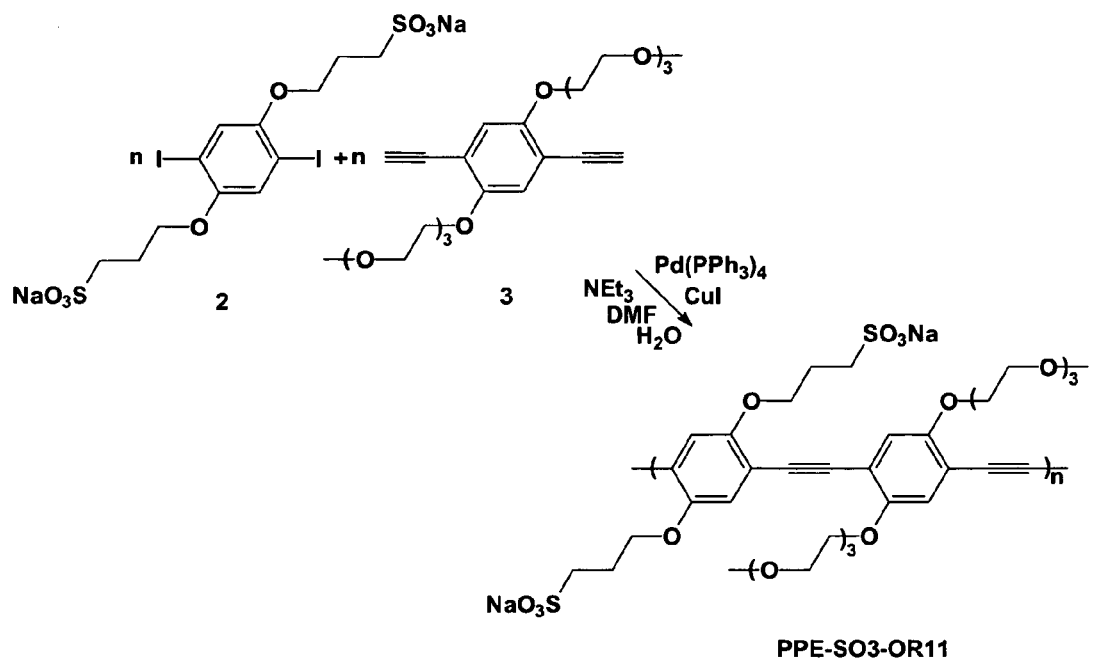
FIG. 2 shows the polymerization of two monomers to prepare a CPE with anionic side groups and oligo(ethylene oxide) side groups, according to an embodiment of the invention.

As shown in FIG. 2, a water soluble CPE (PPE-SO3-OR11) was prepared by condensation. Compound 2 (650 mg, 1 mmol), compound 3 (451 mg, 1 mmol), CuI (5.7 mg, 0.03 mmol), and Pd(PPh$_3$)$_4$ (35 mg, 0.03 mmol) were dissolved in a mixture of 30 mL of DMF, 20 mL of water, and 10 mL of triethylamine. The mixture was refluxed overnight. The reaction mixture was concentrated by rotary evaporation and added dropwise into 250 mL of acetone. The precipitate was dissolved in a small amount of Millipore water and treated with 50 mg of NaCN. The polymer was precipitated again in 250 mL of acetone, redissolved in water, filtered through quantitative filter paper, and filtered using a 25 μm glass filter. The solution was dialyzed against water using 6-8 kD MWCO cellulose membrane. The solution was concentrated via rotary evaporation and the polymer was precipitated with acetone. The precipitate was collected by centrifugation and washed with acetone. The product was a yellow powder and it was dried under vacuum for 5 hours. $^1$H NMR (300 MHz, D$_2$O): δ 2.21 (br), 3.06 (br), 3.26 (br), 3.41 (br), 3.50 (br), 3.72 (br), 4.15 (br), 6.84 (br).

Polymer solutions with various concentrations ranging between 1.0 and 0.6 g/dL were prepared in DMSO. Following the procedure disclosed in Tan et al., *Adv. Mater.* 2004, 16, 1208-12, the intrinsic viscosity of the polymer was found to be 0.34 dL/g. From this value, the molecular weight of the polymer was estimated to be ~40 kD.

Example 4

The currently accepted value for the number of accessible silanol groups on a glass surface is approximately 5 groups per nm$^2$. Using this value along with the diameter of the silica particles (300 nm or 5 μm), the relationship between surface area and volume of a sphere, and the density of silica (1.96 g/mL), the number of silanol groups per gram of sample can be calculated. Such calculations for the silica particles afford estimates of 13,000 (300 nm) and 197,000 (5 μm) grams of particles per mole of silanol groups. For the surface modification reactions, the number of equivalents of trialkoxysilane to silica particles was calculated based on these equivalent weights. In an effort to investigate the effect of surface graft density of the polymer on the properties of the resulting particles, surface modification reactions were carried out using a different number of equivalents of 1 relative to silanol. In particular, when using 300 nm silica particles for preparation of CPE bound silica SiO2-PPE-1, >50 equivalents of 1 were reacted with the silica particles, for SiO2-PPE-2, 10 equivalents of 1 were used, and for SiO2-PPE-3, 5 equivalents of 1 and 5 equivalents of APTS were used. In the latter sample, APTS was used to introduce non-reactive surface sites to reduce the surface density of the ArI functionality.

Silica particles (200 mg) and compound 1 (63 mg, 0.15 mmol) were mixed in 10 mL of toluene and refluxed for 4 hours. The surface modified silica particles (SiO2-ArI) were collected via centrifugation and washed with acetone several times. The particles were dried under vacuum overnight.

A shown in FIG. 6, 2 (119 mg, 0.184 mmol), 3 (84.7 mg, 0.188 mmol), surface modified silica particles (SiO2-ArI) (50 mg), CuI (1.07 mg, 5.6 μmol), and Pd(PPh$_3$)$_4$ (6.5 mg, 5.6 mop were dissolved in a mixture of 30 mL of DMF, 20 mL of water and 10 mL of triethylamine. The reaction mixture was refluxed overnight. The polymer grafted silica particles (SiO2-PPE-2) were collected via centrifugation and washed with methanol several times. The particles were washed successively with multiple portions of THF, methanol, and water. Methanol and water washes were repeated until the solution exhibited no yellow color with blue fluorescence under UV lamp. Finally, the particles were washed with acetone. The particles were dried under vacuum overnight. A similar procedure was followed for the preparation of SiO2-PPE-4 using 2 (32.5 mg, 0.05 mmol), 3 (22.5 mg, 0.05 mmol), surface modified silica particles (SiO2-ArI) (100 mg), CuI (0.3 mg, 1.5 μmol), and Pd(PPh$_3$)$_4$ (1.7 mg, 1.5 μmol).

The SiO$_2$ surface modification process was monitored by FTIR spectroscopy. The unmodified 5 μm silica particles (SiO2-OH) exhibit a strong peak at 1110 cm$^{-1}$ which is assigned to the Si—O—Si asymmetric stretch. In addition, the characteristic bands at 952, 804, and 475 cm$^{-1}$ are assigned to silanol Si—OH stretch, Si—O—Si symmetric stretch and Si—O—Si bend, respectively. A broad band centered at 3400 cm$^{-1}$ is due to the OH stretch originating from both silanol and adsorbed water. Another broad peak around 1600 cm$^{-1}$ is also due to OH stretch of adsorbed water. The FTIR spectrum of SiO2-ArI gives clear evidence for the presence of the ArI groups. In particular, in addition to the bands seen in the spectrum of SiO$_2$, a series of weak bands at ~2900 cm$^{-1}$ are observed in the IR spectrum of the ArI modified silica particle most likely due to the CH stretches from the amidopropylsilyl group in the SiO2-ArI. Also, multiple weak bands in 1400-1600 region indicate the presence of sp$^3$ and/or sp$^2$ C—C bonds. These observations support the premise that the surface modification with ArI was accomplished by the reaction of SiO$_2$ with 1.

Example 5

In order to confirm the presence of PPE-SO3-OR11 like polymer on the surface of the silica particles following their reaction with the monomers and catalyst, IR spectra of polymer-grafted silica particles (SiO2-PPE-2) and free polymer (PPE-SO3-OR11) were compared. Although the weaker bands in the spectrum of SiO2-PPE-2 are suppressed by the strong band at 1108 cm$^{-1}$, identification of important peaks is still possible. The polymer PPE-SO3-OR11 gives a characteristic band at 1213 cm$^{-1}$ associated with the sulfonate group on the polymer side chain. Although this band is obscured by the strong band at 1108 cm$^{-1}$, an enhanced shoulder around 1210 cm$^{-1}$ can be observed in the spectrum of SiO2-PPE-2. Also, a weak band at 2202 cm$^{-1}$ is indicative of carbon-carbon triple bonds in the backbone of the polymer. The expansion of the spectrum of SiO2-PPE-2 in this region shows a band at 2211 cm$^{-1}$ confirming the presence of the ethynyl bonds in the polymer backbone.

A control experiment was performed in order to validate the covalent attachment of the polymer to the silica surface. Thus, an identical polymerization reaction in the presence of unfunctionalized silica particles (SiO2-OH) instead of aryl iodide modified silica particles (SiO2-ArI) gave free polymer and unmodified silica particles as assessed by the complete absence of the yellow color and fluorescence characteristic of the polymer. This result shows that the presence of aryl iodide functionality is necessary for attachment of the polymer on the silica surface. From this result a conclusion can be made that the polymer is covalently attached to the surface rather than being physisorbed. Also, comparison of the loading levels of polymer on samples SiO2-PPE-2 and -3 indicates that the amount of aryl iodide on the surface is important for covalent attachment of polymer onto the silica surface (see below). Silica particles of 5-μm diameter (SiO2-PPE-4) were modified according to the same procedure used for the 300 nm particles. These larger size particles were convenient for analyses by scanning electron microscopy (SEM) and confocal fluorescence microscopy.

Example 6

Thermogravimetric analysis (TGA) was used to estimate the loading levels of the polymer on the silica particles by comparison to the TGA traces from unfunctionalized silica particles and the PPE grafted particles. Several qualitative trends are evident in the TGA data. First, the unmodified particles exhibit approximately a 4% weight loss over the 250-700° C. temperature range. This weight decrease arises from loss of strongly adsorbed water and dehydration of residual silanol units. Each of the surface modified samples exhibits a greater weight loss with temperature; this increased loss is associated with the presence of organic material on the particle surfaces. The thermally-induced weight loss in the TGA increases along the series SiO2-ArI<SiO2-PPE-3<SiO2-PPE-2<SiO2-PPE-1, indicating that the amount of surfaced-grafted organic (polymer) material increases along the same series. As indicated above in Example 4, the three samples of SiO2-PPE were prepared in an effort to vary the loading level of PPE on the surface. In particular, the reaction conditions were adjusted so as to increase the surface loading of the reactive ArI units in the order SiO2-PPE-3<SiO2-PPE-2<SiO2-PPE-1. Thus, the TGA results show a direct correlation between the initial loading of ArI reactive groups, and the amount of polymer that is grafted onto the particle surfaces.

Calculations were carried out to estimate the thickness of the grafted polymer layer from the TGA data. This calculation was carried out only for SiO2-PPE-1, which was prepared using the SiO2-ArI sample with the highest surface concentration of reactive ArI units. Based on the TGA analysis, the thickness of the polymer-graft layer on the SiO2-PPE-1 particles was estimated to be 12 nm. Since the length of a polymer repeat unit (PRU) of a similar conjugated polymer (PPE-SO3) has been estimated by molecular modeling to be ~1.2 nm, the thickness of the polymer-graft layer corresponds to approximately 10 PRU.

Example 7

Electron microscopy was used to observe the changes in the surface texture of the particles caused by surface grafting of the polymer. Transmission electron microscope (TEM) images of unfunctionalized silica particles (SiO2-OH) show the smooth surface of the particles. The TEM images of the 300 nm particles with the polymer surface graft layer clearly exhibit a rough surface texture, which we associate with the presence of the polymer on the surface. It is noted that the TEM images do not show a significant change in the size of the particles after grafting polymer on the surface. This finding is consistent with the TGA results, which suggest that on average the graft layer is approximately 12 nm in thickness. Although the particle size was not affected, the TEM data suggests that the 300 nm particles are uniformly coated with a thin layer of polymer on the surface. Scanning electron microscope (SEM) images of 5 μm SiO$_2$ unmodified particles exhibit a very smooth uniform surface texture. By contrast, the particles which are surface grafted exhibit an "orange peel" like surface texture that appears to be associated with the CPE bound to the surface. The image suggests that much of the surface is covered with the grafted layer; however, the covering is clearly non-uniform. There is evidence for large aggregates of a thickness of about 50 nm on the surface. The origin of this material is unclear. One possibility is that it is material that was initially produced in solution during the polymerization, and then became chemically or physically adsorbed to the surface.

Example 8

Confocal fluorescence microscope images of the 5 μm SiO$_2$ particles with the surface grafted polymer (SiO2-PPE 4) clearly show the green fluorescence from the polymer on the surface of the particles, which confirms the electron microscopy results which suggest that the polymer is grafted to the surface of the particles. The images also indicate that although there is emission from the entire surface of the particle, there appear to be regions in which there is a "clustering" of the fluorescent material. This finding correlates with the SEM image of the surface of a 5 µm particle, which suggests that the polymer graft layer has a non-uniform texture or thickness. In addition to the apparent non-uniformity of the fluorescence from the particle surfaces, the confocal images also suggest that the particles have a propensity to aggregate in the suspension, as evidenced by the predominance of particle clusters in the images rather than isolated single particles.

Example 9

The synthesis of a CPE surface functionalized silica particle was carried out as illustrated in FIG. 11, using a CPE, PPE-NMe3-OR8-COOH, as formed in the manner shown in FIG. 10, and subsequently condensed with functionality introduced to the silica surface by a silane coupling agent. In a flask was combined 181 mg (0.25 mmol) of monomer 5 (2,5-diiodo-1,4-bis(3-(N,N,N-trimethylammonium)propoxy)benzene, dichloride), 91 mg (0.25 mmol) of 4 (1,4-diethynyl-2,5-bis[2-(2-methoxyethoxy)ethoxy]benzene), 3 mg (0.0125 mmol) of 4-iodobenzoic acid, 20 mL of DMF, 12.5 mL of diisopropyl amine, and 12.5 mL of water, under a nitrogen atmosphere. Separately a catalyst solution was prepared by combining 8.8 mg of $PdCl_2(PPh_3)_2$ and 2.3 mg of CuI in 5 mL of DMF and the solution deoxygenated by bubbling Ar gas through the solution. The catalyst solution was injected into the flask containing the monomer solution and the mixture was maintained at 70° C. overnight. The mixture was concentrated by rotary evaporation. The concentrated solution was added to 50 mL of acetone dropwise to precipitate the CPE, PPE-NMe3-OR8-COOH. The precipitated PPE-NMe3-OR8-COOH was dissolved in water and filtered using quantitative filter paper, and subsequently filtered using a 25 µm glass filter. The filtered solution was dialyzed against water using a 6-8 kD MWCO cellulose membrane. The solution was concentrated by rotary evaporation and the polymer was precipitated with acetone, centrifuged and washed with additional acetone. The PPE-NMe3-OR8-COOH was dried under vacuum for 5 hours to yield a yellow powder.

To silica particle which were surface treated aminopropyltrimethoxylsilane was added PE-NMe3-OR8-COOH with DCC and DMAP in DMF as shown in FIG. 11. Amidation between the surface amines and the terminal carboxylic acid groups yielded the surface grafted CPE, SiO2-PPE-NMe3-OR8.

Example 10

The solution photophysical properties of PPE-type CPEs are strongly affected by the nature of solvent. In a good solvent, such as methanol, the polymer chains are well solvated and they exhibit photophysical properties characteristic of excitons confined to a single chain. On the other hand, in a poor solvent, such as water, the polymer chains tend to aggregate. Aggregation results in π-π stacking between chains, and due to the increased interchain interactions the aggregated polymers exhibit bathochromic shifts of both absorption and emission.

The properties of the surface grafted polymers were characterized relative to the absorption and fluorescence of PPE-SO3-OR11 in methanol and water. The results are summarized in Table 1, below, and the optical spectra shown in FIG. 12. As can be seen in FIG. 12, a 30 nm bathochromic shift of the absorption maximum is observed upon switching the solvent from methanol to water, a phenomenon consistent with other known PPE-type CPEs where it is attributed to aggregation of the polymer chains in water. The effect of aggregation in water has a more significant effect on the fluorescence properties of the polymer. In methanol, the fluorescence spectrum appears as a narrow band with $\lambda_{max}=467$ nm with a shoulder at ~500 nm. In water, on the other hand, the emission profile becomes broader and is red-shifted compared to that seen in methanol. In addition to the spectral shift, the fluorescence quantum efficiency decreases from 0.39 to 0.26.

TABLE 1

Photophysical Properties of PPE-SO3-OR11

| Solvent | $\lambda_{max}$ (nm) | $\epsilon$ (M$^{-1}$cm$^{-1}$) | $\lambda_{em}$ (nm) | Φ |
|---|---|---|---|---|
| Methanol | 439 | 22,100 | 467 | 0.39 |
| Water | 468 | 21,900 | 484 | 0.26 |

Suspensions of CPE-grafted silica particles in methanol and water also exhibit strong fluorescence. As shown in FIG. 12, the fluorescence of the surface grafted particles (SiO2-PPE-2) appears as a very broad, structureless band, with $\lambda_{max}=535$ nm. The fluorescence from the polymer-grafted particles is red-shifted compared to that of PPE-SO3-OR11 in water, a feature which suggests that the polymer is strongly aggregated on the surface of the silica. Attempts were made to measure the absorption spectra of suspensions of the polymer grafted silica particles; however, the spectra were strongly distorted in the near-UV region due to light scattering. The scattering also precluded measurement of the fluorescence quantum efficiency of the particles. Although direct measurement of the absorption spectra of the grafted-particles was not possible, the absorption profile could be approximated by the fluorescence excitation spectrum of a particle suspension in methanol. As shown in FIG. 12, the excitation spectrum is very similar to the absorption spectrum of the free polymer. The $\lambda_{max}$ of excitation was found to be 415 nm, which is slightly blue shifted from that of free polymer in methanol. This blue shift in the excitation spectrum may arise because on average the length of the surface grafted polymer is lower compared to that of the solution polymerized polymer.

Example 11

CPEs exhibit the property of amplified quenching, whereby the fluorescence of the polymer is quenched by oppositely charged quencher ions with very high efficiency. Amplified quenching is attributed to very efficient static quenching which occurs within an ion pair complex formed between the quencher ion and the CPE. The quenching efficiency is also augmented by the ability of the fluorescent (singlet) exciton to diffuse rapidly within a CPE chain and among aggregated chains. Estimates based on ultrafast spectroscopy suggest that the singlet exciton is quenched by the cyanine energy acceptors with essentially unit efficiency when it is created within a radius of ca. 10 nm from a quencher ion.

To demonstrate the utility of the CPE-grafted silica colloids as signaling elements in fluorescence based bioassays fluorescence quenching profiles were examined for the inventive CPE bound silica particles. The fluorescence quenching properties of the PPE-grafted particles was examined using five different cationic quencher ions including methyl viologen ($MV^{2+}$), $Cu^{2+}$, diethyldicarbocyanine (DEDCC), diethylcyanine (DEC), and diethyl-thiadicarbocyanine (DETDCC). The structures of the quenchers are shown in FIG. 13. Among these quenchers, $MV^{2+}$ and $Cu^{2+}$ act via a charge (electron) transfer quenching mechanism, while the three cyanine dyes quench via the dipole-dipole (Förster) energy transfer mechanism. An important distinction between the two quenching mechanisms is that in order for charge transfer quenching to be efficient, the exciton and quencher ion must be in close proximity (<1 nm separation), whereas quenching via the dipole-dipole mechanism is efficient even when the exciton and quencher are separated by distances greater than 5 nm.

FIG. 14 illustrates the fluorescence quenching data for quenching of SiO2-PPE-2 by $MV^{2+}$ (charge transfer quencher) and DEDCC (energy transfer quencher) and Table 2, below, summarizes the quenching data for all of the quenchers. The premise that the cyanines quench via a dipole-dipole energy transfer mechanism is supported by the quenching data for DETDCC which shows that the DETDCC-induced quenching of the SiO2-PPE-2 fluorescence is accompanied by the appearance of the sensitized fluorescence from DETDCC at 700 nm.

TABLE 2

Summary of $K_{sv}$ Values and Fraction of Accessible Fluorophore for SIO2-PPE-2

| Quencher | $K_{sv}(H_2O)$ | $K_{sv}(MeOH)$ | $f_a$ (%) |
|---|---|---|---|
| $MV^{2+}$ | $4.02 \times 10^6$ | $3.63 \times 10^6$ | 61 ($55^a$, $60^b$) |
| $Cu^{2+}$ | $5.95 \times 10^6$ | $7.33 \times 10^6$ | 70 |
| DEDCC | $5.21 \times 10^6$ | $3.11 \times 10^5$ | >99 |
| DEC | $1.98 \times 10^7$ | $1.25 \times 10^5$ | >99 |
| DETDCC | $2.08 \times 10^{6b}$ | $2.99 \times 10^5$ | >99 |

$^a$SiO2-PPE-1.
$^b$SiO2-PPE-3.

There are several interesting features with respect to the quenching studies of the SiO2-PPE-2 particles. First, all of the quencher ions give rise to very efficient quenching of the fluorescence from the particles; in each case the Stern-Volmer constants ($K_{SV}$) of quenching range from $10^5$ to $10^7 M^{-1}$. This observation indicates that the surface-grafted CPEs exhibit retain the property of amplified quenching, which is a favorable property which may allow the materials to be used in sensor schemes.

A second point of interest is that there is a distinct difference in the overall quenching seen for the quenchers that act by charge transfer ($MV^{2+}$ and $Cu^{2+}$) and by dipole-dipole energy transfer (the cyanine dyes). As exemplified in FIG. 14(a) for quenching by $MV^{2+}$, quenchers that act by the charge transfer mechanism quench only a fraction of the total fluorescence from the SiO2-PPE-2 particles. In particular, addition of $MV^{2+}$ up to c=5 μM leads to quenching of approximately 60% of the SiO2-PPE-2 fluorescence. However, beyond this amount of added $MV^{2+}$ the quenching effect "saturates", i.e., further addition of quencher does not afford additional quenching. Similar saturation behavior has been observed in other fluorescence quenching systems, and a modified Stern-Volmer expression has been developed to model the data, $$\frac{I^o}{(I^o - I)} = \frac{1}{f_a K_{SV}[Q]} + \frac{1}{f_a} \quad (Eq\ 1)$$

where $I^o$ and $I$ are the fluorescence intensity in the absence and presence of quencher, $f_a$ is the fraction of total fluorescence that is quenched, and $K_{SV}$ is the Stern-Volmer quenching constant for the fluorescence component that is quenched. Use of this expression for charge transfer quenching of SiO2-PPE-2 by $MV^{2+}$ and $Cu^{2+}$ affords $K_{SV}$ values in excess of $10^6$ $M^{-1}$, and $f_a \approx 0.6$, indicating that at the limit of high quencher concentration ca. 60% of the total fluorescence intensity is quenched. In contrast to the behavior of the charge transfer quenchers, we find that the cyanine dye energy transfer quenchers quench essentially 100% of the fluorescence emission from SiO2-PPE-2. As exemplified by the data for quenching by DEDCC in FIG. 14(b), in aqueous solution the dye quenches 90% of the SiO2-PPE-2 fluorescence at a concentration of ca. 2 μM with an overall $K_{SV}$ in excess of $10^6$ $M^{-1}$.

The difference in quenching behavior for the energy transfer quenchers (cyanines) and the charge transfer quenchers ($MV^{2+}$ and $Cu^{2+}$) may arises because the PPE-SO3-OR11 graft layer on the surface of the colloids exists in a strongly aggregated state, and that some fraction of the fluorescent polymer excitons are deeply trapped within these aggregates. The fact that the polymer layer exists in a strongly aggregated state presents a steric barrier that prevents the quencher ions from penetrating into some regions of the film. Since the polymer graft layer is on average 5 nm or greater in thickness, and the charge transfer quenchers cannot access the "interior" regions of the graft film, the quenchers are only able to efficiently quench excitons that are in the "exterior" of the graft layer. Importantly, the excitons that are trapped deep within the aggregate structure are not able to be quenched by the charge transfer quenchers, and emission from these trapped excitons is responsible for the "unquenched" fluorescence component. Different behavior is observed for the cyanine dye energy transfer quenchers, because dipole-dipole energy transfer is active and efficient even when the exciton-quencher separation distance is in excess of 5 nm. Thus, in this case, even though the aggregate excitons are trapped within the graft layer, long distance dipole-dipole energy transfer still occurs, leading to effective quenching of the fluorescence from the PPE-grafted particles with increasing cyanine dye concentration.

The Stern-Volmer quenching efficiencies for the cyanine dyes are an order of magnitude larger for aqueous suspensions compared to suspensions in methanol. This effect arises because the solubility of the cyanine dyes is considerably lower in water compared to methanol. As a result the dye-SiO2-PPE-2 association constant is considerably larger, which leads to the much larger quenching efficiency.

Example 12

*Corbetia marina* cultures were grown overnight, 12 to 14 hours, in a marine broth. The cultures, 18 mL aliquots were washed three times with 0.85% NaCl solution where the culture was separated from the wash solutions by centrifugation and removal of the liquid using a pipette. Each washed culture was diluted to 2 mL with 0.85% NaCl solution and the culture suspensions were separated into four samples of 500 μL. The deoxygenation of some samples was carried out by bubbling argon through the suspension for 15 minutes. Surface grafted CPE beads were added to the samples where 50 μL of a suspension of the beads was added to 0.5 mL of the samples to yield a concentration of $1 \times 10^{-8}$ beads per mL. The samples that were screened for light activated biocidal activity were placed such that the coated beams were approximately 1 cm from a light beam originating from a Fiber Lite 1900 source. The samples were gently shaken for 15 minutes using a Vortex Genie in the presence of the light. Dark biocidal activity was examined using aluminum foil enclosed sample containers, which were shaken for 15 minutes with no light source. All samples examined for light activated and dark activity were blended with 2 μL/mL Syto 60 and Sytox Green dyes prior to mounting the samples on microscope slides that were covered with slips sealed at the edges with immersion oil to minimize the evaporation of water and reduce oxygen exposure. The samples were imaged using confocal fluorescence microscopy.

Samples that were exposed to air and light demonstrated a high level of biocidal activity as opposed to samples that were kept in the dark or were deoxygenated. Deoxygenated samples showed similar ratios of killed and live bacteria regardless of the light exposure experience by the sample. The deoxygenated samples showed significantly less clustering on the surface grafted CPE beads. As shown in FIG. 15, irradiated surface grafted CPE beads resulted in the destruction of a large proportion of *Cobetia marina* cells that contacted the surface grafted CPE. FIG. 15(*a*) shows the light, emitted as green light that corresponds to dead bacteria, which is much more than that emitted as red light, which corresponds to living bacteria, shown in FIG. 15(*b*). The ratio of dead to living bacteria is about 6.3. Interestingly, upon irradiation in the presence of bacteria, agglomeration of the surface grafted CPE beads occurs, as is shown in FIG. 15(*c*). The biocidal activity was also evident for *Cobetia marina* cells that had been exposed to surface grafted CPE beads in the dark. FIG. 16(*a*) shows the light emitted from dead bacteria and FIG. 16(*b*) shows that emitted from living bacteria. The ratio of dead to living bacteria is about 0.08, where only bacteria directly adhering to the surface grafted CPE beads were dead. The agglomeration noted for light activated biocidal surface grafted CPE beads was not observed in the dark.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A biocidal surface grafted cationic conjugated polyelectrolyte comprising:
a solid substrate comprising an amino coupling moiety bonded to a surface of the substrate, and
a cationic conjugated polyelectrolyte comprising a poly(phenylene ethynylene) backbone with cationic side groups on phenyl units thereof and terminal carboxylic acid groups made by combining a cationic group-containing diiodo-benzene monomer, a diethynyl-benzene monomer and 4-iodobenzoic acid in a single solution under conditions sufficient to produce a carboxylic acid group terminated poly(phenylene ethynylene);
wherein the amino group is bonded via an amide linkage to a terminal carboxyl group of the cationic conjugated polyelectrolyte; and wherein the surface grafted conjugated polyelectrolyte exhibits light-activated biocidal properties.

2. The surface grafted conjugated polyelectrolyte of claim 1, wherein said solid substrate is a nanoparticle or a microparticle.

3. The surface grafted conjugated polyelectrolyte of claim 1, wherein said solid substrate comprises a metal oxide, a metal, a semiconductor, carbon, or a polymer.

4. The surface grafted conjugated polyelectrolyte of claim 1, wherein said solid substrate comprises silica or titania particles.

5. The surface grafted conjugated polyelectrolyte of claim 4, wherein said amino coupling moiety further comprises a surface hydroxyl group-bound silyl group linked by a chain of 1 to 12 atoms to the amino moiety.

6. The surface grafted conjugated polyelectrolyte of claim 1, wherein said conjugated polyelectrolyte further comprises oligo(ethylene oxide) side units bonded to phenyl units of the backbone.

7. The surface grafted conjugated polyelectrolyte of claim 1, wherein said substrate comprises a silica particle and said cationic side groups comprise tetralkylammonium cationic groups.

8. The surface grafted conjugated polyelectrolyte of claim 1, wherein said substrate comprises a silica particle and said cationic side groups comprise 4 diazabicyclo[2.2.2]octane cationic groups.

9. A method of preparing the biocidal surface grafted conjugated polyelectrolyte of claim 1, comprising the steps of:
contacting a substrate comprising a surface having reactive sites and a coupling agent comprising a first reactive functionality complementary to said reactive sites of said surface and an amino functionality in a solvent under conditions wherein said reactive sites of said surface react with said first reactive functionality of said coupling agent to produce an amino functionalized substrate; then,
contacting said amino functionalized substrate with a cationic conjugated polyelectrolyte containing at least one terminal carboxyl group under conditions suitable for reaction of the at least one terminal carboxyl group with the amino functionality to form an amide linkage, to provide a biocidal surface grafted conjugated polyelectrolyte, wherein the surface grafted conjugated polyelectrolyte exhibits light-activated biocidal properties,
wherein said cationic conjugated polyelectrolyte containing at least one terminal carboxyl group is made by combining a cationic group-containing diiodo-benzene monomer, a diethynyl-benzene monomer and 4-iodobenzoic acid in a single solution under conditions sufficient to produce a carboxylic acid group terminated poly(phenylene ethenylene) backbone with cationic side groups on phenyl units thereof.

10. The method of claim 9, wherein said coupling agent is aminopropyltrimethoxysilane.

11. The method of claim 10, wherein said conjugated polyelectrolyte comprises

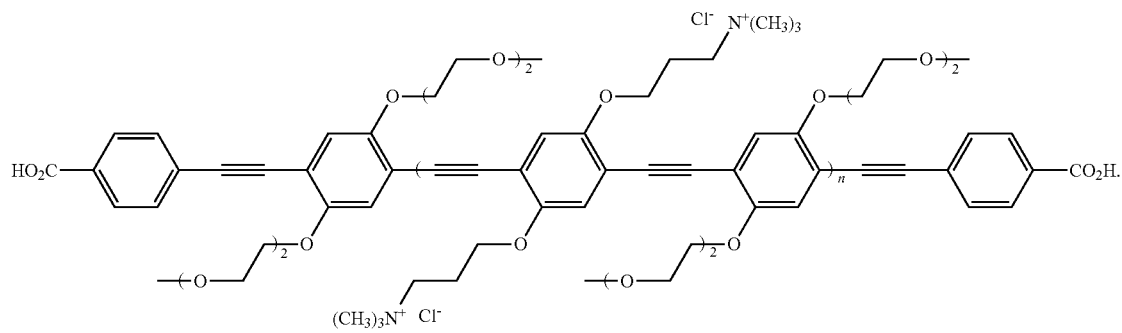

12. A biocide comprising the surface grafted cationic conjugated polyelectrolyte of claim 1, wherein said cationic conjugated polyelectrolyte provides biocidal activity against at least one biological agent in the dark and under illumination.

13. The biocide of claim 12, wherein said biocidal activity that occurs upon irradiation with light is greater than said biocidal activity in the absence of light.

14. The biocide of claim 12 wherein said solid substrate is a nanoparticle or a microparticle.

15. The biocide of claim 12 wherein said solid substrate comprises a metal oxide, a metal, a semiconductor, carbon, or a polymer.

16. The biocide of claim 12 wherein said solid substrate comprises silica or titania particles.

* * * * *

UNITED STATES PATENT AND TRADEMARK OFFICE
CERTIFICATE OF CORRECTION

PATENT NO.        : 8,455,265 B2
APPLICATION NO.   : 12/529390
DATED             : June 4, 2013
INVENTOR(S)       : Whitten et al.

It is certified that error appears in the above-identified patent and that said Letters Patent is hereby corrected as shown below:

On the title page, in column 2, Item (56) under "Other Publications", line 1, delete "B. et al," and insert --B., et al.,--, therefor On title page 2, in column 1, Item (56) under "Other Publications", line 1, delete "B. et al," and insert --B., et al.,--, therefor On title page 2, in column 1, Item (56) under "Other Publications", line 3, delete "G. et al," and insert --G., et al.,--, therefor On title page 2, in column 1, Item (56) under "Other Publications", line 4, delete "Z. et al," and insert --Z., etal.,--, therefor On title page 2, in column 1, Item (56) under "Other Publications", line 7, delete "C. et al," and insert --C., et al.,--, therefor On title page 2, in column 1, Item (56) under "Other Publications", line 8, delete "H. et al," and insert --H., et al.,--, therefor On title page 2, in column 1, Item (56) under "Other Publications", line 10, delete "C. et al," and insert --C., et al.,--, therefor On title page 2, in column 1, Item (56) under "Other Publications", line 11, delete "Q.-L. et al, et al," and insert --Q. L., et al.,--, therefor On title page 2, in column 1, Item (56) under "Other Publications", line 12, delete "L. et al," and insert --L., et al.,--, therefor On title page 2, in column 1, under "Other Publications", line 13, delete "E. et al," and insert --E., et al.,--, therefor Signed and Sealed this
Sixth Day of May, 2014

Michelle K. Lee
*Deputy Director of the United States Patent and Trademark Office*

CERTIFICATE OF CORRECTION (continued)
U.S. Pat. No. 8,455,265 B2

On title page 2, in column 2, Item (56) under "Other Publications", line 1, delete "K. et al," and insert --K., et al.,--, therefor On title page 2, in column 2, Item (56) under "Other Publications", line 2, delete "J. et al, Angewante" and insert --J., et al., Argewandte--, therefor On title page 2, in column 2, Item (56) under "Other Publications", line 4, delete "X. et al," and insert --X., et al.,--, therefor On title page 2, in column 2, Item (56) under "Other Publications", line 5, delete "X.-L. et al," and insert --X. L., et al.,--, therefor On title page 2, in column 2, Item (56) under "Other Publications", line 6, delete "K. et al," and insert --K., et al.,--, therefor On title page 2, in column 2, Item (56) under "Other Publications", line 7, delete "W. et al," and insert --W., et al.,--, therefor On title page 2, in column 2, Item (56) under "Other Publications", line 8, delete "al," and insert --al.,--, therefor On title page 2, in column 2, Item (56) under "Other Publications", line 10, delete "P.-Z. et al," and insert --P. Z., et al.,--, therefor On title page 2, in column 2, Item (56) under "Other Publications", line 11, delete "N. et al," and insert --N., et al.,--, therefor In the Claims In column 18, line 20, in claim 7, delete "tetralkylammonium" and insert --tetraalkylammonium--, therefor In column 18, line 24, in claim 8, delete "4 diazabicyclo" and insert --4-diazabicyclo--, therefor In column 18, line 47, in claim 9, delete "ethenylene" and insert --ethynylene--, therefor In column 18, line 52, in claim 11, delete "comprises" and insert --comprises:--, therefor